United States Patent [19]

Spivack et al.

[11] Patent Number: 4,709,050
[45] Date of Patent: Nov. 24, 1987

[54] SUBSTITUTED-(HYDROXYPHENYL)-PYR-ROLIDINE-2,5-DIONE STABILIZERS

[75] Inventors: John D. Spivack, Spring Valley; Stephen D. Pastor, Yonkers, both of N.Y.

[73] Assignee: Ciba-Geigy Corporation, Ardsley, N.Y.

[21] Appl. No.: 798,660

[22] Filed: Nov. 15, 1985

[51] Int. Cl.$^4$ ............... C07D 207/12; C07D 207/24
[52] U.S. Cl. .................................. 548/520; 548/521; 548/545; 524/104; 524/105
[58] Field of Search .................. 548/545, 520, 521

[56] References Cited

U.S. PATENT DOCUMENTS

| | | | |
|---|---|---|---|
| 3,627,780 | 12/1971 | Bonnard et al. | 548/521 |
| 3,790,597 | 2/1974 | Dexter et al. | 548/520 |
| 4,067,895 | 1/1978 | Hofer et al. | 548/545 X |
| 4,111,901 | 9/1978 | Hechenbleikner | 548/520 X |
| 4,206,076 | 6/1980 | Hofer et al. | 548/545 X |
| 4,456,716 | 6/1984 | Spivack et al. | 548/545 X |

OTHER PUBLICATIONS

Bruszewski, C. A.; 93:8013x, (1980).
Dudley, et al.; C. A., 82:51270p, (1975).
Horning, et al.; C. A., 80:2248lm (1974).

*Primary Examiner*—Joseph Paul Brust
*Attorney, Agent, or Firm*—Harry Falber

[57] ABSTRACT

Substituted-(hydroxyphenyl)-pyrrolidine-2,5-dione derivatives of the formula

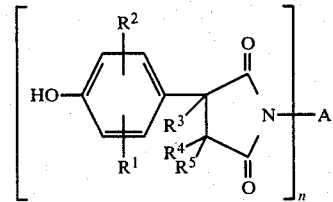

are prepared by the reaction of the appropriate maleimide and phenolic compounds and are useful as stabilizers for organic polymers.

8 Claims, No Drawings

SUBSTITUTED-(HYDROXYPHENYL)-PYRROLIDINE-2,5-DIONE STABILIZERS

Organic polymeric materials such as plastics and resins, are subject to thermal, oxidative and photodegradation. A great variety of stabilizers are known in the art for stablizing a diversity of substrates. Their effectiveness varies depending upon the causes of its degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

It has now been determined that the (hydroxyphenyl)-pyrrolidine-2,5-dione derivatives of this invention exhibit a variety of desirable properties which makes them particularly effective and useful as stabilizers. The compounds show excellent activity in protecting polyolefins, high impact polystyrene, rubbers such as polybutadiene and styrene-butadiene rubber, and other elastomers wherein retention of elasticity and inhibition of crosslinking, crazing, discoloration, odor formation and exudation are basic requirements.

U.S. Pat. No. 4,456,716 discloses (hydroxyphenylthio)-imide stabilizers which are structurally distinct in the nature of the sulfur linking group and in the substitution pattern.

In addition, Chemical Abstracts 93:8013 X (1980), Chemical Abstracts 86:65291r (1976), Chemical Abstracts 80:2248lm (1973) and Chemical Abstracts 76:107806p (1971) disclose N-substituted derivatives of aryl succinic acid imides wherein only substituent on the aryl group is hydroxyl. These compounds are all noted for their pharmacological activity.

It is the primary object of this invention to provide a class of pyrrolidine-2,5 dione derivatives which exhibit a broad range of improved stabilization performance characteristics.

Various other objects and advantages of this invention will become evident from the following description thereof.

The compounds of this invention correspond to the formula

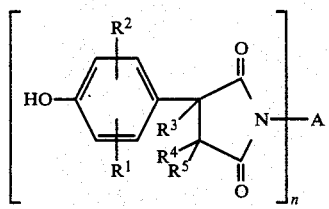

wherein
$R^1$ and $R^2$ independently are alkyl of 1 to 12 carbon atoms, cycloalkyl of 5 to 6 carbon atoms, phenyl or phenyl substituted by alkyl of 1 to 12 carbon atoms;
$R^3$, $R^4$ and $R^5$ independently are hydrogen, alkyl of 1 to 3 carbon atom or

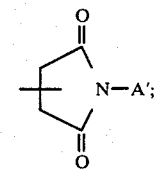

n is 1 or 2;
A, when n is 1, is alkyl of 1 to 30 carbon atoms, phenyl, cycloalkyl of 5 to 6 carbon atoms or
A, when n is 2, is alkylene of 1 to 10 carbon atoms, phenylene, cycloalkylene of 5 to 6 carbon atoms or diphenylene ($C_1$–$C_3$) alkylene; and

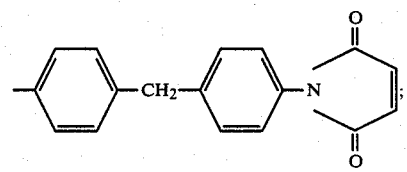

A' is alkyl of 1 to 30 carbon atoms, phenyl, cycloalkyl of 5 to 6 carbon atoms or

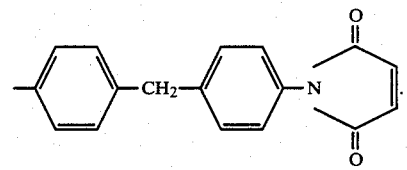

Preferred compounds within the above structure are those wherein $R^1$ is in the ortho position to the hydroxyl group in the phenyl ring.

The $R^1$ and $R^2$ groups are preferably straight-chain or branched alkyl with 1 to 8 carbon atoms, such as methyl, n-butyl, sec-butyl, tert-butyl, tert-pentyl, 2-ethylhexyl, n-octyl and tert-octyl. The groups tert-butyl, tert-pentyl and tert-octyl are especially preferred. Also especially preferred is for the $R^2$ group to be in the ortho position to the hydroxy group, particularly if $R^2$ is tert-alkyl.

The substituents on the phenyl in $R^1$ and $R^2$ are preferably alkyl of 1 to 8 carbon atoms. $R^3$, $R^4$ and $R^5$ are preferably hydrogen or

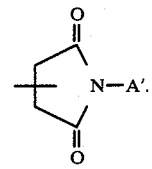

A and A' are preferably alkyl of 1 to 18 carbon atoms, particularly methyl, n-butyl, dodecyl and octadecyl; phenyl; and, for A, alkylene of 1 to 6 carbon atoms.

The derivatives of this invention can be prepared by reacting the appropriately substituted maleimide with an alkylated phenol in a solvent to yield the desired products. The solvent can be an aromatic hydrocarbon such as benzene, toluene, xylene, and the like, or a heterocyclic ether, such as tetrahydrofuran, optionally in the presence of an aliphatic alcohol co-solvent such as tert.butyl alcohol and the like. The reaction temperature ranges from −10° to 50° C. The preferred method for preparing the compounds of this invention involves reacting the maleimide with the phenol in the presence of a proton acceptor such as a tertiary amine including triethylamine or pyridine, or a metal hydride such as sodium or lithium hydride. The starting materials needed to prepare the stabilizers of this invention are items of commerce or can be prepared by known methods. For example, preparative methods for preparing cyclic imides are described in Hargreaves, Pritchard and Dave, Chemical Reviews, 70, 439–469 (1970).

The compounds of the present invention are particularly effective in stabilizing organic materials subject to oxidative, thermal and actinic degradation, such as plastics, polymers and resins.

Substrates in which these compounds are particularly useful are polyolefins such as polyethylene and polypropylene; polystyrene, including impact polystyrene, ABS resin, SBR, isoprene, as well as natural rubber, polyesters including polyethylene terephthalate and polybutylene terephthalate, including copolymers, and lubricating oils such as those derived from mineral oil.

In general polymers which can be stabilized include:

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or α-methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for minstance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadien, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl-butyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamid or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as blockcopolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

In general, the compounds of the formulae I and II of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example, 2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example,
2,2'-methylene-bis-(6-tert.butyl-4-methylphenol)
2,2'-methylene-bis-(6-tert.butyl-4-ethylphenol)
2,2'-methylene-bis-$\alpha$4-methyl-6-($\alpha$-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-($\alpha$-methylbenzyl)-4-nonylphenol]
2,2'-methylene-bis-[6-($\alpha,\alpha$-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl)-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrat]
di-(3-tert.butyl-4-hydroxy-5-methylphenyl)-dicyclopentadien
di-[2-(3'-tert.butyl-2'-hydroxy-5'-methyl-benzyl)-6-tert.-butyl-4-methylphenyl]-terephthalate.

1.5. Benzyl compounds, for example,
1,3,5-tri-(3,5-di-tert.butyl-4-hydroxybenzyl)-2,4,6-trimethylbenzene-di-(3, 5-di-tert.butyl-4-hydroxybenzyl)-sulfide
3,5-di-tert.butyl-4-hydroxybenzyl-mercapto-acetic acid isooctyl ester
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphoric acid di-octadecyl ester
3,5-di-tert.butyl-4-hydroxybenzyl-phosporic acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbaminate 1.7. Esters of $\beta$-(3,5-di-tert.butyl-4-hydroxyphenyl)-propionic acid with monohydric or polyhydric alcohols, for example,
methanol
octadecanol 1,6-hexanediol
neopentylglycol
thiodiethyleneglycol
diethyleneglycol
triethyleneglycol
pentaerythritol
tris-hydroxyethyl isocyanurate
di-hydroxyethyl oxalic acid diamide 1.8. Ester of β-(5-tert.butyl-4-hydroxy-3-methylphenyl)-propionic acid with monohydric or polyhydric alcohols, for example,
methanol
octadecanol
1,6-hexanediol
neopentylglycol
thiodiethyleneglycol
diethyleneglycol
triethyleneglycol
pentaerytritol
tris-hydroxyethyl isocyanurate
di-hydroxyethyl oxalic acid diamide 1.9. Amides of β-(3,5-di-tert.butyl-4-hydroxyphenyl)-propionic acid for example,
N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine 2. UV absorbers and light stabilisers 2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3',5'-di-tert.-butyl-, 5-chloro-3'-tert.butyl-5'-methyl-, 3'-sec.butyl-5'-tert.butyl-, 4'-octoxy, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Ester of optionally substituted benzoic acids for example, phenyl salicylate, 4-tert.butyl-phenylsalicilate, octylphenyl salicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol, such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl)-sebacate bis-(1,2,2,6,6-pentamethylpiperidyl)-sebacate n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylendiamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethyl-piperazinone).

2.7. Oxalic acid diamides, for example, 4,4'-di-octyloxyoxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis (3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy- as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythrit diphosphite, tris-(2,4-di-tert.butylphenyl) phosphite, di-isodecylpentaerythritol diphosphite, di-(2,4-di-tert.butylphenyl)pentaerythritol diphosphite, tristearylsorbite triphosphite, tetrakis-(2,4-di-tert.butylphenyl)-4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilisers, for example copper salts in combination with iodides and/or phosphorus compounds and salts of divalent manganese.

7. Basic co-stabilisers, for example, melamine, polyvinyl-pyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

The following examples illustrate the embodiment of this invention. In these examples, all parts given are by weight unless otherwise specified.

EXAMPLE 1

3-(3,5-di-tert-butyl-4-hydroxyphenyl)-1-n-butyl-pyrrolidine-2,5-dione

To a solution of sodium tert-butoxide prepared from 2.40 g (0.1 mol) of sodium hydride and 135 ml of tert-butyl alcohol is added dropwise a solution of 20.63 g (0.1 mol) of 2,6-di-tert-butylphenol in 100 ml of tert-butyl alcohol. The reaction mixture is stirred at room temperature for 150 minutes and then to the resultant green solution is added dropwise over 120 minutes a solution of 15.31 g (0.1 mol.) of N-n-butylmaleimide in 50 ml of tert-butyl alcohol. The reaction mixture is stirred at room temperature overnight and is then mixed with 10 ml of glacial acetic acid. The reaction mixture is poured into 1.5 l of water and the resultant mixture is extracted twice with chloroform. The organic extracts are combined and dried over anhydrous sodium sulfate. The solvent is removed in vacuo and the residue is purified by flash chromatography (3:1 heptane:toluene eluent) to give 4.25 g (12%) of a white solid: mp 109°–112° C.;

Anal. Calcd for $C_{22}H_{34}NO_3$: C, 73.3; H, 9.5; N, 3.9. Found: C, 73.5; H, 9.6; N, 3.8.

EXAMPLE 2

3-(3,5-di-tert-butyl-4-hydroxyphenyl)-4-(1-n-butyl-2,5-dioxopyrrolidin-3-yl)-1-n-butylpyrrolidine-2,5-dione This compound is prepared by the procedure of Example 1 from 2.40 g (0.1 mol) of sodium hydride, 20.63 g (0.1 mol) of 2,6-di-tert-butyl-phenol and 15.31 g (0.1 mol) of N-n-butylmaleimide in dimethyl sulfoxide. The residue is extracted with a 1:1 mixture of hot heptane containing 10 ml of toluene. The heptane extract is concentrated to 150 ml and the resultant solid collected by filtration. The crude product is recrystallized from cyclohexane to give 1.03 g (4%) of a white solid: mp 151°–153° C.

Anal. Calcd for $C_{30}H_{44}N_2O_5$: C, 70.3: H, 8.6; N, 5.5. Found: C, 70.4; H, 8.7; N, 5.4.

EXAMPLE 3

3-(3,5-di-tert-butyl-4-hydroxyphenyl)-1-methyl-pyrrolidine-2,5-dione.

This compound is prepared by the procedure of Example 1 from 2.40 g (0.1 mol) of sodium hydride, 20.63 g (0.1 mol) of 2,6-di-tert-butylphenol, and 11.11 g (0.1 mol) of N-methylmaleimide in tert-butyl alcohol. The residue is recrystallized from petroleum ether to give 13.2 g (42%) of crude product. The analytical sample is prepared by flash chromatography (1:1 heptane:ethyl acetate eluent) followed by trituration with a mixture of heptane and toluene to give 3.0 g of a white solid: mp 164°–166° C.

Anal. Calc for $C_{19}H_{27}NO_3$: C, 71.7; H, 8.9; N, 4.4. Found: C, 71.6; H, 8.7; N, 4.7.

EXAMPLE 4

3-(3,5-di-tert-butyl-4-hydroxyphenyl)-1-n-dodecylpyrrolidine-2,5-dione

This compound is prepared by the procedure of Example 1 from 2.40 g (0.1 mol) of sodium hydride, 20.63 g (0.1 mol) of 2,6-di-tert-butylphenol, and 26.54 g (0.1 mol) of N-n-dodecylmaleimide in tert-butyl alcohol. The reaction mixture is concentrated in vacuo and the residue is dissolved in 800 ml of toluene. The toluene solution is extracted sequentially with 1M sodium hydroxide (2×100 ml) and water (6×200 ml). The organic phase is dried over anhydrous sodium sulfate. The solvent is removed in vacuo and the residue purified by flash chromatography (8:2 heptane: ethyl acetate eluent) followed by recrystallization from petroleum ether to give 8.15 g (17%) of a white solid: mp 66°–70° C.

Anal. Calcd for $C_{30}H_{49}NO_3$: C, 76.4; H, 10.5; N, 3.0. Found: C, 76.4; H, 10.1; N, 3.1.

EXAMPLE 5

3-(3-tert-butyl-4-hydroxy-5-methylphenyl)-1-n-dodecylpyrrolidine-2,5-dione

This compound is prepared by the procedure of Example 1 from 1.20 g (50 mmol) of sodium hydride, 8.21 g (50 mmol) of 2-tert-butyl-6-methylphenol, and 13.27 g (50 mmol) of N-n-dodecylmaleimide in tert-butyl alcohol. The residue is purified by preparative HPLC (8:2 heptane:ethyl acetate eluent) to give 4.70 g (22%) of a yellow wax.

Anal. Calcd for $C_{27}H_{43}NO_3$; C, 75.5; H, 10.1; N, 3.3. Found: C, 75.4; H, 10.5; N, 3.5.

EXAMPLE 6

3-(3,5-di-tert-butyl-4-hydroxyphenyl)-1-n-octadecylpyrrolidine-2,5-dione

This compound is prepared by the procedure of Example 1 from 2.40 g (0.1 mol) of sodium hydride, 20.63 g (0.1 mol) of 2,6-di-tert-butylphenol, and 34.96 g (0.1 mole) of N-n-octadecylmaleimide in tert-butyl alcohol. The residue is purified by dry-column chromatography (3:1 heptane:ethyl acetate eluent) followed by recrystallization from petroleum ether to give 20.5 g (37%) of a white solid: mp 70°–73° C.

Anal. Calcd. for $C_{36}H_{61}NO_3$: C, 77.8; H, 11.1; N, 2.5. Found: C, 78.0; H, 11.1; N, 2.7.

EXAMPLE 7

3-(3,5-di-tert-butyl-4-hydroxyphenyl)-1-phenylpyrrolidine-2,5-dione

This compound is prepared by the procedure of Example 1 from 2.40 g (0.1 mol) of sodium hydride, 20.63 g (0.1 mol) of 2,6-di-tert-butylphenol, and 17.32 g (0.1 mol) of N-phenylmaleimide in tetrahydrofuran. The reaction mixture is concentrated in vacuo and the residue is dissolved in 150 ml of toluene. The toluene solution is extracted sequentially with 1M sodium hydroxide (2×100 ml) and water (2×50 ml). The organic phase is dried over anhydrous sodium sulfate and then the solvent is removed in vacuo. The residue is triturated with petroleum ether to give 0.78 g (2%) of white crystals: mp 204° C.

Anal. Calcd. for $C_{24}H_{29}NO_3$: C, 76.0; H, 7.7; N, 3.7. Found: C, 76.0; H, 7.8; N, 3.8.

EXAMPLES 8 AND 9

The procedure of Example 1 is repeated using 0.80 g (0.1 mol) of lithium hydride, 20.63 g (0.1 mol) of 2,6-di-tert-butylphenol, and 17.90 g (50 mmol) of 1,1'-(methylene-di-1,4-phenylene) bismaleimide in tetrahydrofuran. The residue is purified by preparative HPLC (6:4 heptane:ethyl acetate eluent) to give two major components.

The lower R_f component, 4-maleimido-4'-[3-(3,5-di-tert-butyl-4-hydroxyphenyl) succinimido]-diphenylmethane (Example 8) is isolated to give 1.50 g (5%) of a yellow solid: mp 120°–125° C.

Anal. Calcd for $C_{35}H_{36}N_2O_5$: C, 74.5; H, 6.4; N, 4.9. Found: C, 74.4; H, 6.5; N, 4.9.

The higher R_f component, 4,4'-bis[3-(3,5-di-tert-butyl-4-hydroxyphenyl)succinimido] diphenylmethane (Example 9) is isolated to give 1.00 g (3%) of a yellow solid: mp 135°–140° C.

Anal. Calcd for $C_{49}H_{58}N_2O_6$: C, 76.3; H, 7.6; N, 3.6. Found: C, 76.2; H, 7.8; N, 3.7.

EXAMPLE 10

3-(3,5-dimethyl-4-hydroxyphenyl)-3-(1-noctadecyl-2,5-dioxopyrrolidin-3-yl)-1-n-octadecylpyrrolidine-2,5-dione Diasteriomers of the above are prepared by the procedure of Example 1 from 2.40 g (0.1 mol) of sodium hydride, 12.22 g (0.1 mol) of 2,6-dimethylphenol, and 34.96 g (0.1 mol) of N-n-octadecylmaleimide in tert-butyl alcohol. The residue is purified by preparative HPLC (4:1 heptane:ethyl acetate eluent) to give two major components.

The lower R_f component is isolated to give 2.90 g (7%) of a white solid: mp 84°–86° C.

Anal. Calc for $C_{52}H_{88}N_2O_5$: C, 76.0; H, 10.8; N, 3.4. Found: C, 75.9; H, 10.8; N, 3.5.

The higher R_f component is isolated to give 2.30 g (6%) of a white solid: mp 90°–94° C.

Anal. Calcd for $C_{52}H_{88}N_2O_5$: C, 76.0; H, 10.8; N, 3.4. Found: C, 76.2, H, 11.2; N, 3.4

EXAMPLE 11

1,6-bis[3-(3,5-di-tert-butyl-4-hydroxyphenyl)-2,5-dioxopyrrolidin-1-yl]hexane.

To a solution of 14.95 g (72.4 mmol) of 2,6-di-tert-butylphenol in 200 ml of tetrahydrofuran at 5° C. is added dropwise 45 ml (72.4 mmol) of 1.6M solution of n-butyl-lithium in hexane. After stirring for 15 minutes at room temperature, 10.0 g (36.2 mmol) of N,N'-(1,6-hexanediyl)bis-(maleimide) are added slowly over a period of 4 hours using a powder-addition funnel. The reaction mixture is acidified with a solution of 2.5 g of concentrated hydrochloric acid in 10 ml of tetrahydrofuran. The reaction mixture is filtered and then concentrated in vacuo. The residue is purified by preparative HPLC (7:3 heptane:ethyl acetate eluent) to give 0.3 g (1%) of a light yellow solid: mp 190°–193° C.

Anal. Calcd for $C_{42}H_{60}N_2O_6$: C, 73.2; H, 8.8, N, 4.1. Found: C, 72.5; H, 8.4; N, 4.2.

EXAMPLE 12

Unstabilized polypropylene powder (Hercules Profax 6501) is thoroughly blended with the indicated amount of additive. The blended materials are then milled on a two roll mill at 182° C. for five minutes after which time the stabilized polypropylene is sheeted from the mill and allowed to cool. The milled polypropylene is then cut into pieces and compression molded on a hydraulic press at 220° C. and 175 psi ($1.2 \times 10^6$ Pa) into 5 mil (0.127 mm) films. The samples are exposed in a fluorescent sunlight/black light chamber until failure. Failure is taken as the hours required to reach 0.5 carbonyl absorbence by infrared spectroscopy on the exposed films.

| Additive Compound of | Additive Concentration (% by weight) | FS/BL Test Results (Hours to Failure) |
| --- | --- | --- |
| None | — | 130 |
| Example 1 | 0.2 | 270 |
| Example 2 | 0.2 | 270 |
| Example 3 | 0.2 | 260 |
| Example 4 | 0.2 | 280 |
| Example 5 | 0.2 | 230 |
| Example 6 | 0.2 | 290 |
| Example 7 | 0.2 | 260 |
| Example 8 | 0.2 | 190 |

EXAMPLE 13

The procedure of Example 12 is repeated except that plaques of 25 mil (0.635 mm) thickness are prepared. The plaques are exposed to air in a forced draft oven at 150° C. The plaques are considered to have failed on showing the first signs of decomposition (e.g., cracking or brown edged).

| Additive Compound of | Additive Concentration | Oxidative Stability Time to Failure (Hours) |
| --- | --- | --- |
| Example 1 with 0.3% DLTDP | 0.1 | 50 |
| Example 2 with 0.3% DLTDP | 0.1 | 70 |
| Example 3 with 0.3% DLTDP | 0.1 | 60 |
| Example 4 | 0.2 | 30 |
| Example 4 with 0.3% DLTDP | 0.1 | 100 |
| Example 5 | 0.2 | 30 |
| Example 5 with 0.3% DLTDP | 0.1 | 1340 |
| Example 6 | 0.2 | 80 |
| Example 6 with 0.3% DLTDP | 0.1 | 470 |
| Example 7 with 0.3% DLTDP | 0.1 | 50 |
| Example 8 | 0.2 | 50 |
| Example 8 with 0.3% DLTDP | 0.1 | 520 |

DLTDP-dilaurylthiodipropionate

EXAMPLE 14

This example illustrates the stabilization of acrylonitrile-butadiene-styrene (ABS) copolymer by the compounds of this invention. The testing procedure is as follows:

The antioxidant is dissolved in toluene and emulsified in water using Triton X-100 (Rohm & Haas) as a surfactant. The resultant emulsion is mixed well with ABS copolymer containing 40% butadiene (rubber). Steam coagulation of the emulsion/latex mixture yields 40% rubber stabilized ABS crumbs which are then dried at 80° C. for 30 minutes in a fluidized bed drier. The resultant crumbs are combined with styrene-acrylonitrile pellets on a two-roll mill for six minutes. The resultant 15% rubber-containing ABS milled sheet is compression molded at 205° C. into 60 mil plaques which are die cut into 1"×3" specimens. The sample plaques are then oven aged at 150° C. and the angle to break is monitored (ASTM D747). This consists of applying a set load through an angle with one stationary point and one moveable point, flexing the sample. The angle is monitored for several aging periods until the specimen breaks.

| Additive (0.225%) | Angle to Break (Oven Aged Samples) | | | |
|---|---|---|---|---|
| | 0 | 30 Min. | 45 Min. | 60 Min. | 90 Min. |
| Base | NB | NB | 50 | — | — |
| Example 1 | NB | NB | — | 89 | — |
| Example 4 | NB | NB | — | 53 | — |
| Example 6 | NB | NB | NB | NB | 49 |

NB = No Break.

These data in Examples 12–14 thus indicate the effective stabilization activity of the instant compounds.

Summarizing, it is seen that this invention provides novel compounds which exhibit effective stabilization activity. Variations may be made in proportions, procedures and materials without departing from the scope of the invention as defined by the following claims.

What is claimed is:

1. A compound of the formula

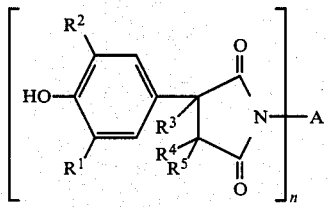

wherein

R¹ and R² independently are alkyl of 1 to 12 carbon atoms, cycloalkyl of 5 to 6 carbon atoms, phenyl or phenyl substituted by alkyl of 1 to 12 carbon atoms;

R³, R⁴ and R⁵ are hydrogen and one of R³, R⁴ and R⁵ is

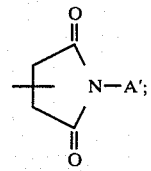

in is 1 or 2;

A, when n is 1, is alkyl of 1 to 30 carbon atoms, phenyl, cycloalkyl of 5 to 6 carbon atoms or

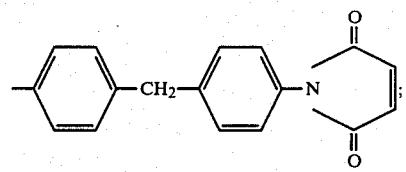

A, when n is 2, is alkylene of 1 to 10 carbon atoms, phenylene, cycloalkylene of 5 to 6 carbon atoms or diphenylene $(C_1-C_3)$alkylene; and A' is alkyl of 1 to 30 carbon atoms, phenyl, cycloalkyl of 5 to 6 carbon atoms or

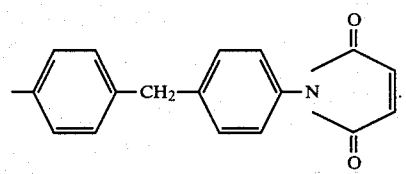

2. The compound of claim 1, wherein R¹ is alkyl of from 1 to 8 carbon atoms.

3. The compound of claim 2, wherein R¹ is tert.-butyl, tert.-pentyl or tert.-octyl.

4. The compound of claim 1, wherein R² is tert.-alkyl of from 4 to 8 carbon atoms.

5. The compound of claim 1, wherein A and A' independently are alkyl of 1 to 18 carbon atoms, alkylene of 1 to 6 carbon atoms or phenyl.

6. 3-(3,5-di-tert-butyl-4-hydroxyphenyl)-4-(1-n-butyl-2,5-dioxopyrrolidin-3-yl)-1-n-butylpyrrolidine-2,-5-dione according to claim 1.

7. 3-(3,5-dimethyl-4-hydroxyphenyl)-3-(1-n-octadecyl-2,5-dioxopyrrolidin-3-yl)-1-n-octadecylpyrrolidine-2,5-dione according to claim 1.

8. The compound of claim 1, wherein A is alkylene of 1 to 6 carbon atoms.

* * * * *